United States Patent
Ichihara

(10) Patent No.: US 7,840,255 B2
(45) Date of Patent: Nov. 23, 2010

(54) X-RAY CT APPARATUS AND MYOCARDIAL PERFUSION IMAGE GENERATING SYSTEM

(75) Inventor: Takashi Ichihara, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 974 days.

(21) Appl. No.: 11/075,701

(22) Filed: Mar. 10, 2005

(65) Prior Publication Data

US 2005/0277830 A1    Dec. 15, 2005

(30) Foreign Application Priority Data

Jun. 11, 2004 (JP) ............................ P2004-174364
Jan. 13, 2005 (JP) .............................. P2005-5977

(51) Int. Cl.
*A61B 5/05* (2006.01)

(52) U.S. Cl. ................... 600/425; 600/407; 600/431

(58) Field of Classification Search ............... 600/410, 600/425, 407, 431, 504, 508
See application file for complete search history.

(56) References Cited

U.S. PATENT DOCUMENTS

| | | | | |
|---|---|---|---|---|
| 4,438,495 | A * | 3/1984 | Collins et al. | 382/131 |
| 4,483,342 | A * | 11/1984 | Pfeifer | 600/425 |
| 6,196,715 | B1 * | 3/2001 | Nambu et al. | 378/197 |
| 6,628,743 | B1 | 9/2003 | Drummond et al. | |
| 6,721,590 | B2 * | 4/2004 | Ohishi et al. | 600/431 |
| 6,745,066 | B1 * | 6/2004 | Lin et al. | 600/425 |
| 6,783,203 | B2 * | 8/2004 | Fujimori | 347/15 |
| 6,891,918 | B2 * | 5/2005 | Drummond et al. | 378/5 |
| 6,898,453 | B2 * | 5/2005 | Lee | 600/407 |
| 2001/0056233 | A1 * | 12/2001 | Uber et al. | 600/431 |
| 2003/0097076 | A1 * | 5/2003 | Nambu et al. | 600/504 |
| 2003/0174804 | A1 * | 9/2003 | Bulkes et al. | 378/8 |

(Continued)

FOREIGN PATENT DOCUMENTS

JP    2003-116843    4/2003

(Continued)

OTHER PUBLICATIONS

WO 2005/013827, Philips, Device and Method if imaging from the heart.*

(Continued)

*Primary Examiner*—Brian Casler
*Assistant Examiner*—Peter Luong
(74) *Attorney, Agent, or Firm*—Oblon, Spivak, McClelland, Maier & Neustadt, L.L.P.

(57) ABSTRACT

An X-ray CT apparatus 1 for radiating X-ray to a subject P so as to scan the subject P and reconstructing a image within the subject P based on an obtained projection data comprises an image generating unit and a blood-flow image generating unit 24e. The image generating unit generates the image based on the projection data in a state in which a concentration of a contrast medium in a myocardial portion of a subject P continuously injected the contrast medium can be considered to be constant. The blood-flow image generating unit 24e generates a blood flow image by removing components of a myocardial tissue from a portion of a myocardial region of the image generated by the image generating unit.

14 Claims, 8 Drawing Sheets

U.S. PATENT DOCUMENTS

2004/0062351 A1* 4/2004 Yoshioka .................. 378/98.8

FOREIGN PATENT DOCUMENTS

WO    WO 2005/013827 A1    2/2005

OTHER PUBLICATIONS

V. Rasche, et al., "ECG-gated 3D-rotational coronary angiography (3DRCA)", Computer Assisted Radiology, XP-008035484, 2002, pp. 827-831.

Ganapathy Krishnamurthi, et al., "Reproducibility of physiologic parameters obtained using functional computed tomography in mice", Proceedings of the SPIE, The International Society for Optical Engineering, vol. 5369, No. 1, XP-002344669, Apr. 2004, pp. 394-405.

Keith M. Stantz, et al., "In Vivo Regional Myocardial Perfusion Measurements in a Porcine Model by ECG-Gated Multi-Slice Computed Tomography", vol. 5031, XP-002344670, pp. 222-233.

U.S. Appl. No. 12/044,432, filed Mar. 7, 2008, Ichihara.

U.S. Appl. No. 12/123,776, filed May 20, 2008, Ichihara, et al.

* cited by examiner

X-RAY CT APPARATUS AND MYOCARDIAL PERFUSION IMAGE GENERATING SYSTEM

CROSS REFERENCES TO RELATED APPLICATIONS

The present application relates to and incorporates by reference Japanese Patent application No. 2004-174364 filed on Jun. 11, 2004 and reference Japanese Patent application No. 2005-005977 filed on Jan. 13, 2005.

BACKGROUND OF THE INVENTION

1. Field of the Invention

The present invention relates to an X-ray CT(computed tomography) device and a myocardial perfusion image generating system for taking contrast CT images such as coronary arterial contrast CT images, myocardial contrast CT images, and so forth, by continuously injecting a contrast medium, and generating a myocardial perfusion image using the obtained contrast CT images.

2. Description of the Related Art

With a myocardial contrast examination using an X-ray CT apparatus, a contrast medium is injected into a subject that is a patient, and contrast CT images are collected. Subsequently, moving images of coronary arteries, endocardial lumen wall, and so forth, are generated from the collected contrast CT images, and are employed for diagnosis.

Also, a blood flow dynamic state (perfusion) examination of the myocardium and a perfusion examination regarding organs such as within a brain tissue have been performed using an X-ray CT apparatus. With these perfusion examinations, attempting to generate a perfusion image by analyzing dynamic contrast CT data obtained from dynamic imaging by bolus injection for injecting a contrast medium in a short period has been conventionally studied.

However, normally, such perfusion imaging is not an isolated examination, but performed as part of a contrast examination. For example, in the event of a myocardial perfusion image, scanning for heart function analysis such as coronary arteries and endocardial lumen movement is also performed as well as scanning of a myocardial perfusion image. Accordingly, it takes a long time for scanning of a myocardial perfusion image, and a examination method resulting in increase of X-ray dosages for the subject ray is hardly acceptable, and accordingly, long-period dynamic imaging using an X-ray CT apparatus has never come into practical use so far. With a perfusion examination regarding capillaries within a brain tissue in light of such a background, a contrast medium is injected into a subject at a time, and images are taken in a short period (see Japanese Unexamined Patent Application Publication No. 2003-116843, for example). More specifically, the contrast medium is injected using a technique such that a temporal peak is formed in the concentration variation of the contrast medium to be inserted into a subject, and imaging with an X-ray CT apparatus is performed synchronously with the timing at which the contrast medium moves to a capillary within a brain tissue. Subsequently, information regarding perfusion is obtained using CT images obtained by imaging using the X-ray CT apparatus based on the temporal concentration variation of the contrast medium in the capillary within the brain tissue.

However, with a conventional technique for obtaining information regarding perfusion by injecting the contrast medium into a subject at a time, the X-raying period of the subject can be suppressed as well as the amount of time for imaging, but additional X-ray imaging is necessary for collecting data for organs other than perfusion, such as coronary artery images and heart function analysis data. Accordingly, further reduction in the shooting period is required.

Furthermore, the number of times of contrast-medium injection and the amount of injection increase as the imaging time increases, since scanning is performed for taking of myocardial perfusion images and myocardial images, respectively. However, the amount of injection of the contrast medium as to a subject has an upper limit, and consequently, the amount of time for imaging and the number of times thereof are also restricted. Accordingly, this presents a problem in that it is difficult to secure long imaging time for myocardial perfusion images.

SUMMARY OF THE INVENTION

Accordingly, the present invention has been made in light of the conventional situations, and it is an object of the present invention to provide an X-ray CT apparatus and a myocardial perfusion image generating system for generating a myocardial perfusion image in a short period while reducing the amount of injection of a contrast medium as to a subject and dosage due to X-ray.

In an aspect, to achieve the object, the present invention provides an X-ray CT apparatus for radiating X-ray to a subject so as to scan the subject and reconstructing a image within the subject based on an obtained projection data, comprising: an image generating unit generating the image based on the projection data in a state in which a concentration of a contrast medium in a myocardial portion of a subject continuously injected the contrast medium can be considered to be constant ; and a blood-flow image generating unit generating a blood flow image by removing components of a myocardial tissue from a portion of a myocardial region of the image generated by the image generating unit.

Furthermore, an X-ray CT apparatus comprises a determining region unit determining the portion of the myocardial region of the image generated by the image generating unit, wherein the blood-flow image generating unit is configured so as to remove the components of the myocardial tissue from the portion of the myocardial region determined by the determining region unit.

Furthermore, the image generating unit is configured so as to generate the blood flow image by subtracting a CT value equivalent to the myocardium from a CT image of the portion of the myocardial region.

Furthermore, an X-ray CT apparatus comprises a display processing unit setting a value of a window level at the time of performing at least either gradation conversion processing and color tone conversion processing based on a value corresponding to the myocardial portion contrasted by the contrast medium and a value corresponding to the myocardium.

Furthermore, an X-ray CT apparatus comprises a display processing unit setting a value of a window level at the time of performing at least either gradation conversion processing and color tone conversion processing so as to emphasize pixels having a value between a value corresponding to the myocardial portion contrasted by the contrast medium and a value corresponding to the myocardium.

Furthermore, in an aspect, to achieve the object, the present invention provides an X-ray CT apparatus comprising: a contrast-medium injector continuously injecting a contrast medium into a subject and obtaining a state in which a concentration of the contrast medium in a myocardial portion of the subject can be considered to be constant; an image collection unit collecting a contrast CT image synchronously with an electrocardiogram during a period in which the concentration of the contrast medium in the myocardial portion can be considered to be constant; and a blood-flow image generating unit generating a blood flow image by subtracting a CT value of the myocardium from the contrast CT image data of the myocardial portion.

Furthermore, in an aspect, to achieve the object, the present invention provides a myocardial perfusion image generating system comprising: an image acquisition unit acquiring an image in a state in which a concentration of a contrast medium in a myocardial portion of a subject continuously injected the contrast medium can be considered to be constant; and a blood-flow image generating unit generating a blood flow image by removing components of a myocardial tissue from a portion of a myocardial region of the image acquired by the image acquisition unit.

Furthermore, in an aspect, to achieve the object, the present invention provides a myocardial perfusion image generating system comprising: an image acquisition unit acquiring contrast CT image data collected synchronously with an electrocardiogram in a period in which a concentration of a contrast medium in a myocardial portion of a subject can be considered to be constant; and a blood-flow image generating unit generating a blood flow image by subtracting a CT value of the myocardium from the contrast CT image data acquired by the image acquisition unit.

Such an X-ray CT apparatus and a myocardial perfusion image generating system according to the present invention generate a myocardial perfusion image in a shorter time while reducing the amount of injection of a contrast medium to a subject, as well as X-ray dosage.

DESCRIPTION OF THE PREFERRED EMBODIMENTS

An X-ray CT apparatus and a myocardial perfusion image generating system according to the present invention will now be described in further detail below with reference to embodiments in conjunction with the accompanying drawings.

Figure 1:
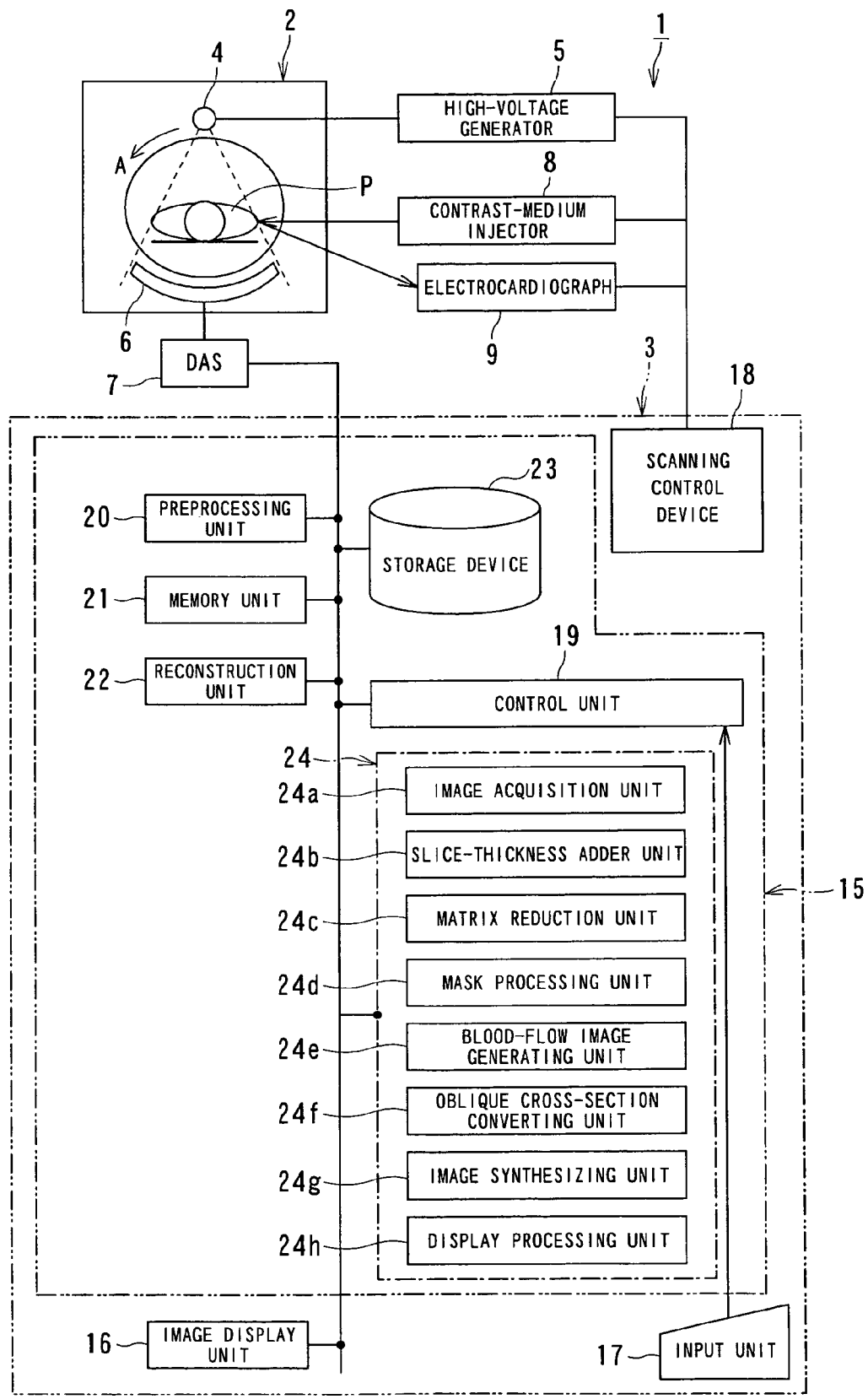
FIG. 1 is a configuration diagram illustrating an X-ray CT apparatus according to an embodiment of the present invention.

FIG. 1 is a configuration diagram illustrating an X-ray CT apparatus according to an embodiment of the present invention. An X-ray CT apparatus 1 comprises a gantry unit 2 and a computer device 3. The gantry unit 2 includes an X-ray tube 4, high-voltage generator 5, X-ray detector 6, DAS (Data Acquisition System) 7, contrast-medium injector 8, and electrocardiograph 9. The X-ray tube 4 and X-ray detector 6 are mounted at positions facing each other sandwiching a subject P in an unshown rotating ring consecutively rotating at a high speed.

The contrast-medium injector 8, which is controlled by a control signal from the computer device 3, has a function for continuously injecting a contrast medium into the subject P in accordance according to certain conditions. The contrast-medium injector 8 can control the amount and concentration of the contrast medium to be injected into the subject P based on the behavior of the contrast medium within the subject P.

Figure 2:
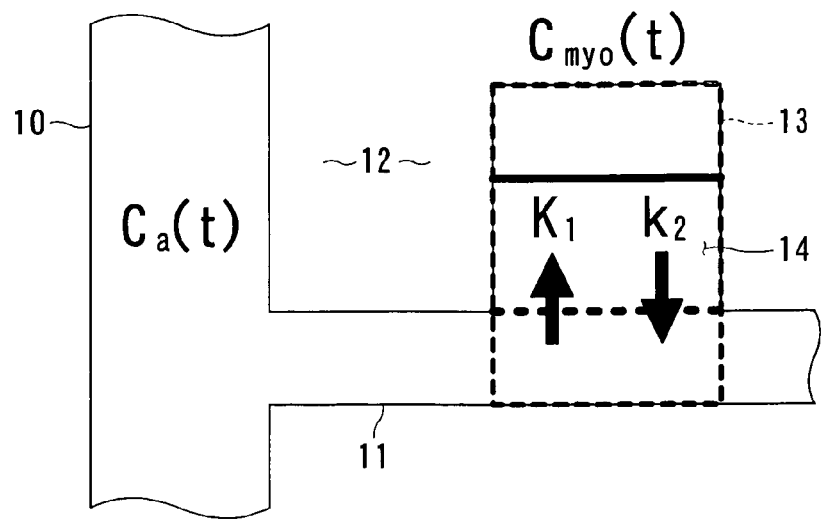
FIG. 2 is a diagram illustrating a model of the behavior of a contrast medium in the heart, within the myocardium, and within a coronary artery of a subject.

FIG. 2 is a diagram illustrating a model of the behavior of a contrast medium in the heart, within the myocardium, and within a coronary artery of a subject. The unshown aorta branches off to a coronary artery 10, and the coronary artery 10 further branches off to a capillary 11, within the subject P. The capillary 11 is introduced into the myocardium 12, and the myocardium 12 comprises the capillary 11 and a myocardial cell 13. The myocardial cell 13 includes a region referred to as a framework 14, and is configured such that the blood can move in and out between the framework 14 and the capillary 11.

Consequently, when a contrast medium is injected into the subject P, the contrast medium is led from the aorta to the coronary artery 10 along with the blood, and led from the coronary artery 10 to the capillary 11. Furthermore, when the contrast medium flows along with the blood within the capillary 11, and reaches the myocardial cell 13, part of the contrast medium flows in the framework 14 within the myocardial cell 13 from the capillary 11. Moreover, the part of the blood flowed in the framework 14 within the myocardial cell 13 flows out of the myocardial cell 13 and moves in the capillary 11 again.

Accordingly, the concentration of the contrast medium in blood within the aorta or coronary artery 10 and the concentration of the contrast medium in blood within the myocardial cell 13 or capillary 11 exhibit different values, and change over time due to movement of the contrast medium. The concentration of the contrast medium in blood within each portion of the subject P is determined by a transitional constant at the time of the contrast medium flowing in the framework 14 within the myocardial cell 13 from the capillary 11, and a transitional constant at the time of the contrast medium flowing in the capillary 11 from the framework 14 within the myocardial cell 13.

More specifically, let us say that the concentration of the contrast medium within the left ventricular lumen or the coronary artery in time t is $Ca(t)$, a region included in the myocardium 12, which includes the capillary 11 and myocardial cell 13, is a unit region, the concentration of the contrast medium within the blood in the myocardium 12 (the average concentration of the contrast medium within the capillary 11 and myocardial cell 13) is Cmyo(t), a transitional constant at the time of the contrast medium flowing in the framework 14 within the myocardial cell 13 from the capillary 11 is K1, and a transitional constant at the time of the contrast medium flowing out of the capillary 11 to the framework 14 within the myocardial cell 13 is k2, Ca(t) and Cmyo(t) are determined by the transitional constant K1 and the transitional constant k2.

Figure 3:
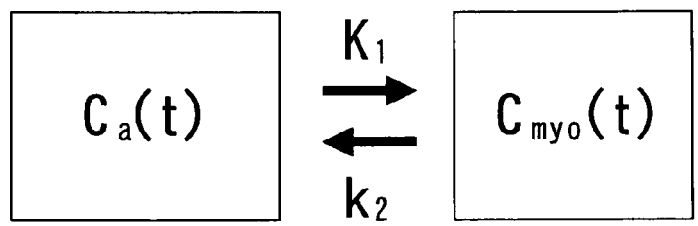
FIG. 3 is a diagram conceptually representing the model illustrated in FIG. 2 using parameters.

FIG. 3 is a diagram conceptually representing the model illustrated in FIG. 2 using parameters. As illustrated in FIG. 3, while the contrast medium having the concentration Ca(t) and the amount proportional to the transitional constant K1 moves in the framework 14 of the myocardial cell 13 from the capillary 11, the contrast medium having the concentration Cmyo(t) and the amount proportional to the transitional constant k2 moves in the capillary 11 from the framework 14 of the myocardial cell 13 at certain time t. Subsequently, the concentration Ca(t) and concentration Cmyo(t) of the contrast medium following movement are determined the transitional constant K1 and transitional constant k2.

Accordingly, the concentration Cmyo(t) of the contrast medium within the myocardium 12 at a certain time t can be represented by the difference between the amount of the contrast medium flowing in the framework 14 and the amount of the contrast medium flowing out of the framework 14, thereby satisfying the following Expression (1).

$$\frac{dCmyo(t)}{dt} = K1 \cdot Ca(t) - k2 \cdot Cmyo(t) \quad (1)$$

On the other hand, heretofore, it has been known that when a contrast medium is injected statically into the subject P in accordance with a certain condition, the concentration of the contrast medium in blood within a coronary artery and the myocardium 12 is considered to be constant.

Figure 4:
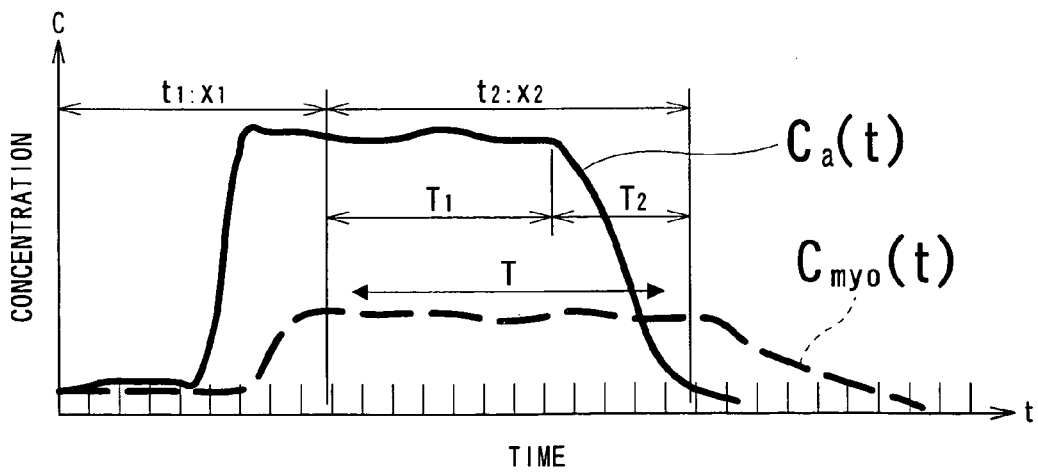
FIG. 4 is a diagram illustrating the temporal concentration variation of a contrast medium in a coronary artery and a myocardial portion due to continuous static injection of the contrast medium into a subject using the contrast-medium injector illustrated in FIG. 1.

FIG. 4 is a diagram illustrating the temporal concentration variation of a contrast medium in a coronary artery and a myocardial portion due to continuous static injection of the contrast medium into a subject using the contrast-medium injector 8 illustrated in FIG. 1.

In FIG. 4, the vertical axis represents concentration C of the contrast medium, and the horizontal axis represents time t. Moreover, the solid line is data indicating change-of-time of the concentration Ca(t) of the contrast medium within the coronary artery, and the dashed line is data indicating change-of-time of the concentration Cmyo(t) of the contrast medium within the myocardial portion made up of the myocardial cell 13 and capillary 11.

As illustrated in FIG. 4, for example, in the event that the contrast medium is continuously injected at an injection speed x1 [cc/sec] for the first t1 second, and then the contrast medium is continuously injected at an injection speed x2 [cc/sec] for the next t2 second, an interval T1 in which the concentration Ca(t) of the contrast medium within the coronary artery is considered to be constant and an interval T in which the concentration Cmyo(t) of the contrast medium within the myocardial region is considered to be constant are obtained. In this example, static injection is performed at injection speed 3 cc/sec for 20 seconds, and subsequently is performed at injection speed 1.5 cc/sec for 30 seconds.

Consequently, in the event that X-ray CT data is collected synchronously with an electrocardiogram at the interval T1 in which the concentration Cmyo(t) of the contrast medium within the myocardial region is considered to be constant, a blood flow image is readily generated with various types of processing using the X-ray CT data following collection. Consequently, the contrast-medium injector 8 is configured so as to inject the contrast medium having a predetermined amount rate per time into the subject P in accordance with a certain condition, and so as to obtain a state in which the concentration Ca(t) and concentration Cmyo(t) of the contrast medium within the coronary artery and myocardial portion are considered to be constant.

Note that the condition for injecting the contrast medium is experientially determined such that the concentration Ca(t) of the contrast medium within the coronary artery becomes constant during collection of X-ray CT data, so some difference exists in injection speed. The recommended conditions such as injection speed at the time of static injection of the contrast medium are described in documents such as "Study of Optimal Contrast Examination Method in Herical Scanning CT", by Atsusi Yamachi and Tadashi Wako, Japan-Germany Medical Reports Vol. 40 No. 2, 1995, for example.

However, there are some cases in which an interval T2 exhibiting the inconstant concentration Ca(t) of the contrast medium within the coronary artery exists in reality as illustrated in FIG. 4. Even in these cases, in the event that a state in which change-of-time of the concentration Ca(t) of the contrast medium within the coronary artery is considered to be constant, and includes linear properties, is satisfied, this can be employed for generation of a blood flow image, and accordingly, the condition of injecting the contrast medium is adjusted using the contrast-medium injector 8 such that change-of-time of the concentration Ca(t) of the contrast medium within the coronary artery becomes constant.

On the other hand, the electrocardiograph 9 is connected to unshown electrodes connected to the subject P. The electrocardiograph 9 has a function to detect an electrocardiogram signal (ECG signal) via the electrodes from the subject P, generate an electrocardiogram of the subject P from the detected ECG signal, and provides this to the computer device 3.

The high-voltage generator 5 is configured so as to supply a tube current or tube voltage to the X-ray tube 4 synchronously with the electrocardiogram in accordance with a control signal from the computer device 3, and so as to detect X-rays transmitting the subject P using the X-ray detector 6, while the concentration Cmyo(t) and Ca(t) of the contrast medium within the coronary artery and the myocardial portion are constant or have linear properties. Furthermore, the X-ray detection signal detected by the X-ray detector 6 is provided to the DAS 7 so as to be digitized, and provided to the computer device 3.

The computer device 3 comprises an image processing device 15, image display unit 16, input unit 17, and scanning control device 18. The scanning control device 18 has a function for providing a control signal to the high-voltage generator 5 and contrast-medium injector 8 to control these devices based on the electrocardiograms collected by the electrocardiograph 9, thereby executing collection of electrocardiogram-synchronous CT images.

Moreover, the image processing device 15 comprises a control unit 19 serving as a core, a preprocessing unit 20 for converting raw data to be output from the DAS 7 into projection data via correction processing and the like, a memory unit 21 for storing the projection data, an image reconstruction unit 22 for reconstructing CT image data from the projection data, a storage device 23 for storing the CT image data, and a myocardial perfusion image generating system 24 for reading the CT image data from the storage device 23 so as to generate a myocardial perfusion image.

The myocardial perfusion image generating system 24 includes an image acquisition unit 24a, slice-thickness adder unit 24b, matrix reduction unit 24c, mask processing unit 24d, blood-flow image generating unit 24e, oblique cross-section converting unit 24f, image synthesizing unit 24g, and display processing unit 24h.

The image acquisition unit 24a includes a function for reading and acquiring myocardial contrast CT image data due to the contrast medium from the storage device 23, and a function for giving the acquired contrast CT image data to the other components of the myocardial perfusion image generating system 24.

The slice-thickness adder unit 24b has a function for receiving myocardial contrast CT image data from the image acquisition unit 24a, and adding the contrast CT values between the adjacent slices or averaging the values, thereby reducing the resolution of the contrast CT image data in the slice direction.

The matrix reduction unit 24c has a function for receiving myocardial contrast CT image data from the image acquisition unit 24a, and subjecting the contrast CT values to adding and averaging, thereby reducing the matrix of the myocardial contrast CT image data.

The mask processing unit 24d has a function for receiving myocardial contrast CT image data from the image acquisition unit 24a, and subjecting the received CT image data to mask processing, thereby extracting a region where the blood flow of the myocardial portion exists. In other words, the mask processing unit 24d serves as a determining region unit for determining a myocardial region portion.

The blood-flow image generating unit 24e has a function for generating a blood flow image in the flow region extracted by the mask processing unit 24d. Now, the method of generating a blood flow image will be described.

As illustrated in FIG. 4, in the event that the concentration Cmyo(t) of the contrast medium within the myocardial portion is considered to be constant, the left side of Expression (1) becomes zero, so Expression (2) can be obtained.

$$\frac{dCmyo(t)}{dt} = 0 \tag{2}$$

Rewriting Expression (1) as Expression (3) from Expression (2), $$K1 \cdot Ca(t) - k2 \cdot Cmyo(t) = 0 \tag{3}$$

Furthermore, modifying Expression (3) obtains Expression (4).

$$K1 = \frac{k2 \cdot Cmyo(t)}{Ca(t)} \tag{4}$$

In Expression (4), in the event that the concentration Ca(t) of the contrast medium within the coronary artery is considered to be constant, under circumstances without necrosis such as no blood flow to the myocardial portion, within several hours following an incidence as to a patient having normal chest pain, the myocardium is alive, and determination is made that k2 is within a normal range, and accordingly, k2 is also considered to be constant as with Ca(t), and the transitional constant K1 is proportional to the concentration Cmyo(t) of the contrast medium within the myocardial portion, as shown in Expression (5).

$$K1 \propto Cmyo(t) \tag{5}$$

Furthermore, with a value representing the fraction of the contrast medium within the blood flow concentration (extraction fraction) as E, and blood perfusion [ml/100 g/min], which is a blood flow rate in unit time and unit weight, serving as the index of perfusion, as F, it has been known that the transitional constant K1 has a relation of K1=E×F.

Accordingly, as illustrated in Expression (6), the concentration Cmyo(t) of the contrast medium within the myocardial portion is proportional to the blood perfusion F within the myocardial portion.

$$Cmyo(t) \propto F \tag{6}$$

That is to say, it is known that the concentration Cmyo(t) of the contrast medium within the myocardial portion indicates the relative value of the blood perfusion F. Accordingly, if the concentration Cmyo(t) of the contrast medium within the myocardial portion can be obtained, the relative value of the blood perfusion F can be known.

Now, the CT value of myocardial contrast CT image data to be obtained by injecting the contrast medium is equal to sum of the CT value of only the myocardium serving as a myocardial tissue component and the CT value of image of a contrast medium component. Accordingly, if the CT value of only the myocardial portion is subtracted from the myocardial contrast CT image data, the concentration Cmyo(t) of the contrast medium within the myocardial portion having a proportional relation to the CT value of image of the contrast medium component can be obtained.

Consequently, the blood-flow image generating unit 24e includes a function for generating the image of the contrast medium component representing the relative value of the blood perfusion F by subtracting the CT value of only the myocardium from the myocardial contrast CT image data in the blood flow region extracted by the mask processing unit 24d as a blood flow image.

Note that in the event that the concentration Ca(t) of the contrast medium within the coronary artery is not considered to be constant, Expression (5) cannot be derived from Expression (4). However, in the event that the change-of-time rate of the concentration Ca(t) of the contrast medium within the coronary artery is constant, or in the event that there are linear properties between the concentration and CT value of the contrast medium, a correction coefficient is obtained based on the change-of-time rate of the contrast medium concentration within this coronary artery, and the image of the contrast medium component can be corrected using the obtained correction coefficient. For example, as shown in Expression (7), let us say that the proportion between the concentration Ca(t) of the contrast medium within the coronary artery at certain time t0 serving as a reference and the concentration Ca(t) of the contrast medium within the coronary artery at time t is a correction coefficient α(t), and correction can be performed by multiplying the CT value of the image of the contrast medium component by the correction coefficient α(t).

$$\alpha(t) = Ca(t)/Ca(t0) \tag{7}$$

Consequently, the blood-flow image generating unit 24e includes a function for obtaining the correction coefficient α(t) so as to correct the image of the contrast medium component in the event that the concentration Ca(t) of the contrast medium within the coronary artery is not constant.

The oblique cross-section converting unit 24f has a function for converting the cross-section of a myocardial blood flow image generated by the blood-flow image generating unit 24e, and generating a cross-sectional image at an arbitrary cross-section, e.g., a circular cross-sectional image with the longitudinal direction of the myocardium serving as an axis thereof.

The image synthesizing unit 24g has a function for synthesizing an image having a high resolution prior to the matrix reduction processing and adding the contrast CT value between slices, i.e., the image data of the mask region of the myocardial contrast CT image data received from the image acquisition unit 24a with the myocardial blood flow image generated by the blood-flow image generating unit 24e so as to generate a synthesized image, and superimposing both images at the same position on a screen, each of which an arbitrary value such as transparency is adjusted so as to display both images.

The display processing unit 24h has a function for providing to the image display unit 16 image signals for displaying the respective images such as blood flow images, oblique cross-sectional images, and synthesized images, which are generated by the blood-flow generating unit 24e, oblique cross-section converting unit 24f, and image synthesizing unit 24g respectively, and a function for setting display conditions so as to visually recognize a blood flow image in each displayed image.

Moreover, the display processing unit 24h is configured so as to display images for instructing the settings of display conditions on the image display unit 16 at the time of setting image display conditions, and also so as to acquire instructions for image display conditions from the input unit 17.

Examples of appropriate image display conditions include a display method for selectively displaying only blood flow images by setting the CT value of the myocardium to the lower limit of pixel values to be displayed, and also setting the value obtained by adding the contrast medium concentration Cmyo(t) in the myocardial portion to the CT value of the myocardium to the upper limit of pixel values to be displayed, and a display method for displaying a portion, which is a range between the CT value of the myocardium and the value obtained by adding the contrast medium concentration Cmyo(t) in the myocardial portion to the CT value of the myocardium in a color corresponding to each pixel value. In this case, an arrangement may be made wherein the upper limit of pixel values can be fine-adjusted due to default values by receiving instructions information from the input unit 17.

Consequently, the display processing unit 24h may include a function for setting a value of a window level at the time of performing at least either gradation conversion and color tone conversion based on a value corresponding to the myocardial portion, and a value corresponding to the myocardium, which are contrasted by the contrast medium, or may include a function for setting a value of window level at the time of performing at least either gradation conversion and color tone conversion so as to emphasize pixels having a value between a value corresponding to the myocardial portion, and a value corresponding to the myocardium, which are contrasted by the contrast medium.

Figure 5:
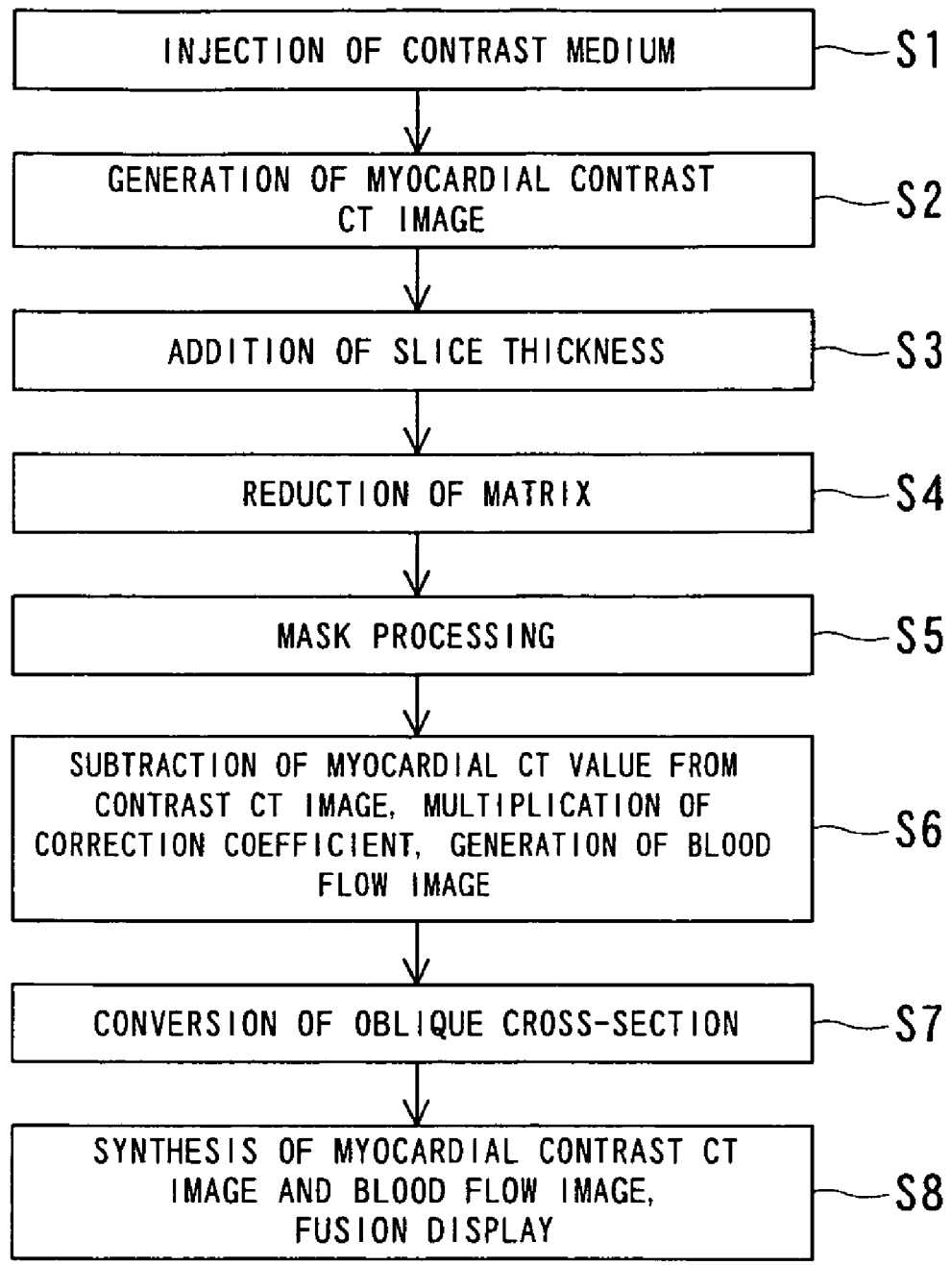
FIG. 5 is a flowchart illustrating a procedures example at the time of generating a myocardial perfusion image using the X-ray CT apparatus illustrated in FIG. 1.

Next, operation of the X-ray CT apparatus 1 will be described. FIG. 5 is a flowchart illustrating a procedures example at the time of generating a myocardial perfusion image using the X-ray CT apparatus 1 illustrated in FIG. 1, wherein reference characters made up of a character S and a number represent each step in the flowchart.

First, in Step S1, the contrast-medium injector 8 is controlled by a control signal from the scanning control device 18, a contrast medium is continuously injected into the subject P in accordance with a certain condition from the contrast-medium injector 8, as illustrated in FIG. 4.

Consequently, the contrast medium concentration Ca(t) within the coronary artery of the subject P becomes a state in which the concentration or the temporal change rate is considered to be constant. Moreover, the contrast medium concentration Cmyo(t) within the myocardial portion becomes a state in which the concentration or the temporal change rate is considered to be constant.

Next, in Step S2, the contrast CT image data of the entire myocardium is collected synchronously with an electrocardiogram during a period in which the contrast medium concentration Cmyo(t) within the myocardial portion is considered to be constant.

More specifically, the electrocardiograph 9 detects an ECG signal via the unshown electrodes bonded to the subject P. The electrocardiograph 9 acquires an electrocardiogram and provides this to the scanning control device 18. The scanning control device 18 provides a control signal to the high-voltage generator 5 based on the electrocardiogram acquired by the electrocardiograph 9. Consequently, the high-voltage generator 5 supplies a tube current and tube voltage to the X-ray tube 4 synchronously with an electrocardiography wave, and X-rays are radiated upon the subject P.

The X-ray detector 6 detects the X-rays radiated upon the subject P and passed through the subject P. An X-ray detection signal output from the X-ray detector 6 is provided to the DAS 7, where digitized raw data is generated. The DAS 7 provides the generated raw data to the preprocessing unit 20, and the preprocessing unit 20 subjects the raw data to preprocessing such as various types of correction processing so as to convert the raw data into projection data. The projection data obtained by the preprocessing unit 20 is temporally stored in the memory unit 21, and then provided to the image reconstruction unit 22. The image reconstruction unit 22 reconstructs CT image data from the projection data, and the reconstructed CT image data is recorded and stored in the storage device 23.

Note that the contrast medium is injected into the subject P, so the CT image data to be stored in the storage device 23 becomes contrast CT image data. The CT image is collected synchronously with an electrocardiogram, so a myocardial contrast axial cross-sectional image can be obtained at the same period of each myocardial portion in a myocardial reduction or expansion period. The image acquisition unit 24a acquires the contrast CT image data stored in the storage device 23, and provides this to the myocardial perfusion image generating system 24.

Furthermore, an axial cross-sectional image set is acquired at each slice of the same cycle in a series of cycles from reduction to expansion of the myocardium for diagnosis of the myocardium as necessary. Various types of image regarding the myocardium, such as a short-axial cross-sectional image, long-axial horizontal tomograph, and long-axial vertical tomograph can be obtained due to the cross-section conversion of the acquired respective axial cross-sectional images.

The myocardial perfusion image generating system 24 can generate a myocardial perfusion image from the myocardial contrast CT image data thus collected and subjected to various cross-section conversion.

Now, attempting to generate a myocardial perfusion image without changing the resolution of the myocardial contrast CT image data may allow influence of noise. Consequently, the myocardial contrast CT image data is subjected to resolution reduction processing as preprocessing of generating a myocardial perfusion image as necessary.

More specifically, in Step S3, the slice-thickness adder unit 24b receives myocardial contrast CT image data from the image acquisition unit 24a, and adds or averages the contrast CT values in the adjacent multiple slices, thereby performing the resolution reduction processing of the contrast CT image data in the slice direction. For example, the slice thickness of the myocardial contrast CT image is normally 0.5 mm or so, so in order to employ the myocardial contrast CT image data for generating a myocardial perfusion image, the resolution in the slice direction is reduced wherein the slick thickness becomes 3 mm, 5 mm, or 10 mm or so.

Furthermore, in Step S4, the matrix reduction unit 24c adds the contrast CT values of the myocardial contrast CT image data in each slice, or averages thereof, thereby performing matrix reduction processing.

Figure 6:
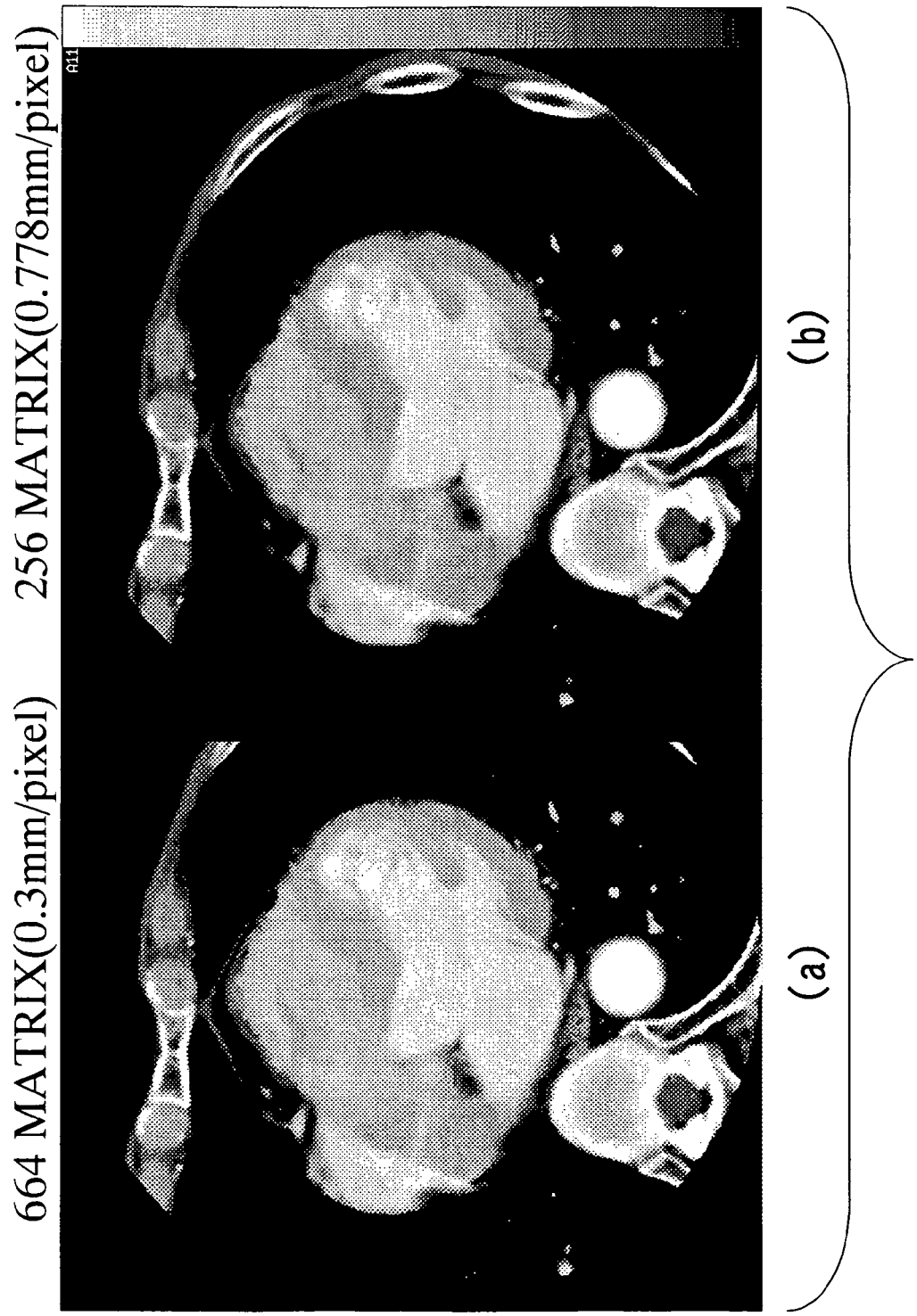
FIG. 6 is a diagram illustrating an image example to be obtained by subjecting myocardial contrast CT image data to matrix reduction processing using the X-ray CT apparatus illustrated in FIG. 1.

FIG. 6 is a diagram illustrating an image example to be obtained by subjecting myocardial contrast CT image data to matrix reduction processing using the X-ray CT apparatus illustrated in FIG. 1.

In FIG. 6, (a) illustrates the myocardial contrast CT image data prior to the matrix reduction processing, and (b) illustrates the myocardial contrast CT image data following the matrix reduction processing.

As illustrated in (a), the myocardial contrast CT image data prior the matrix reduction processing is 664 matrices for example, of which cell size per unit pixel is 0.3 mm. With such a 664-matrix myocardial contrast CT image data, the adjacent or nearby contrast CT values are added or averaged, and 256-matrix myocardial contrast CT image data, of which cell size per unit pixel is 0.778 mm, is obtained, as illustrated in (b). Note that the processing sequence between the slice thickness adding processing and matrix reduction processing may be reverse, i.e., elective.

Next, in Step S5, when the resolution reduction processing is complete, the mask processing unit 24d subjects the myocardial contrast CT image data to masking, thereby extracting regions including the blood flow, of the myocardial contrast CT image data.

Subsequently in Step S6, the blood-flow image generating unit 24e subtracts the CT value of the myocardium from the contrast CT image data included in the regions where the blood flow exists following the masking processing, and a myocardial perfusion image is generated.

Figure 7:
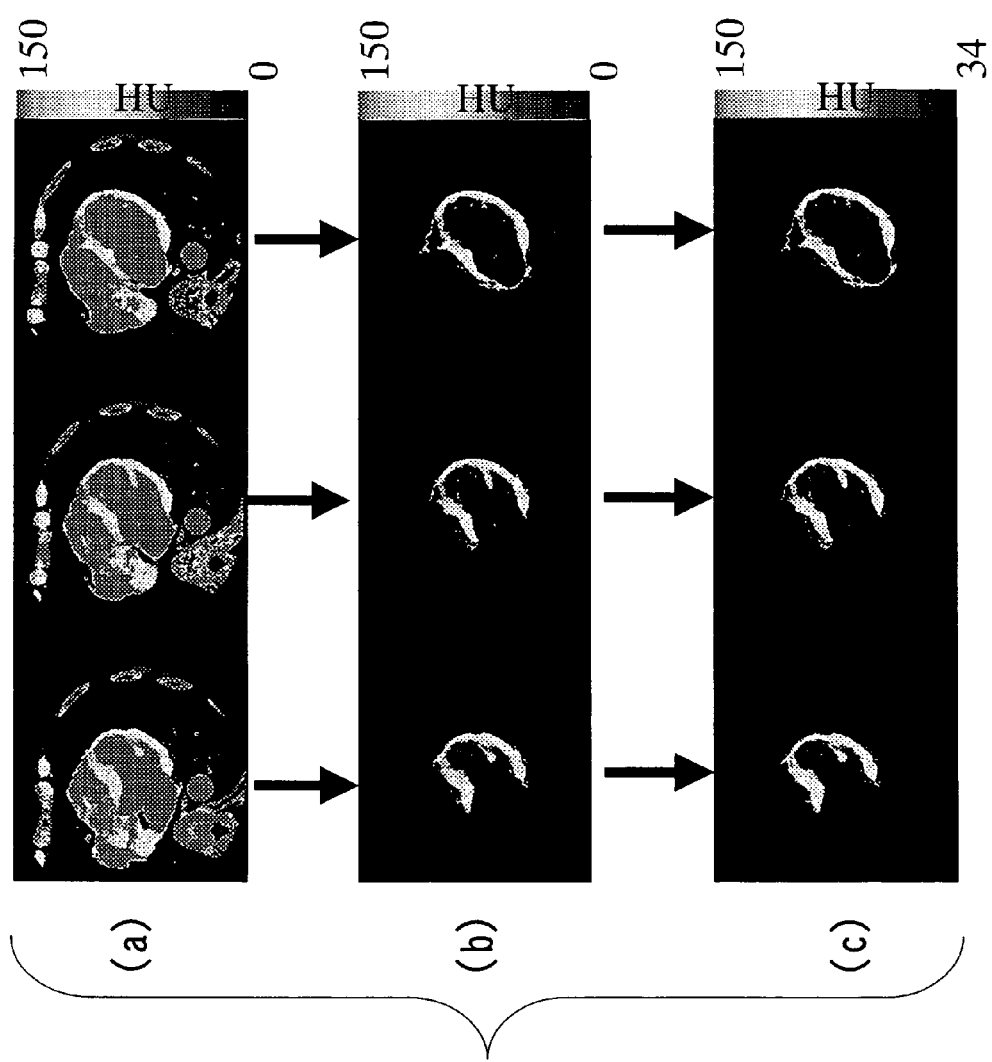
FIG. 7 is a diagram illustrating procedures for generating a myocardial perfusion image from myocardial contrast CT image data using the X-ray CT apparatus illustrated in FIG. 1, and the obtained myocardial perfusion image.

FIG. 7 is a diagram illustrating procedures for generating a myocardial perfusion image from myocardial contrast CT image data using the X-ray CT apparatus illustrated in FIG. 1, and the obtained myocardial perfusion image.

In FIG. 7, (a) is the myocardial contrast CT image data in each slice following the processing of resolution reduction. The mask processing unit 24d subjects the myocardial contrast CT image data such as shown in (a) to masking, the regions including the blood flow such as shown in (b) are extracted. Here, (b) is an example subjected to masking so that the CT values become between 0 and 150 centered on the left ventricle myocardium. The extracted regions including the blood flow can be recognized from (b).

Furthermore, as illustrated in (b), the blood-flow image generating unit 24e executes subtraction of the CT value of the myocardium from the extracted contrast CT image data, thereby obtaining a image of contrast medium component. Moreover, (c) is the image of contrast medium component obtained by the subtraction processing due to the blood-flow image generating unit 24e, i.e., a myocardial perfusion image example wherein the CT value of the myocardium is set to 34, and is subtracted from the contrast CT image data uniformly. This calculation removes myocardial components from the image.

In the event that the contrast medium concentration Ca(t) within the coronary artery is not considered to be constant, the blood-flow image generating unit 24e obtains the correction coefficient α(t) as shown in Expression (7), and multiplies the image of contrast medium component by the correction coefficient α(t) so as to correct the image.

The myocardial perfusion image thus generated is employed for diagnosis. Furthermore, the myocardial perfusion image is subjected to various types of processing for facilitating diagnosis as necessary.

For example, in Step S7, the oblique cross-section converting unit 24f subjects the cross-section of the myocardial perfusion image to conversion processing so as to generate the oblique cross-sectional image of the myocardial fusion image. Note that this Step S7 may be performed following Step S2.

Figure 8:
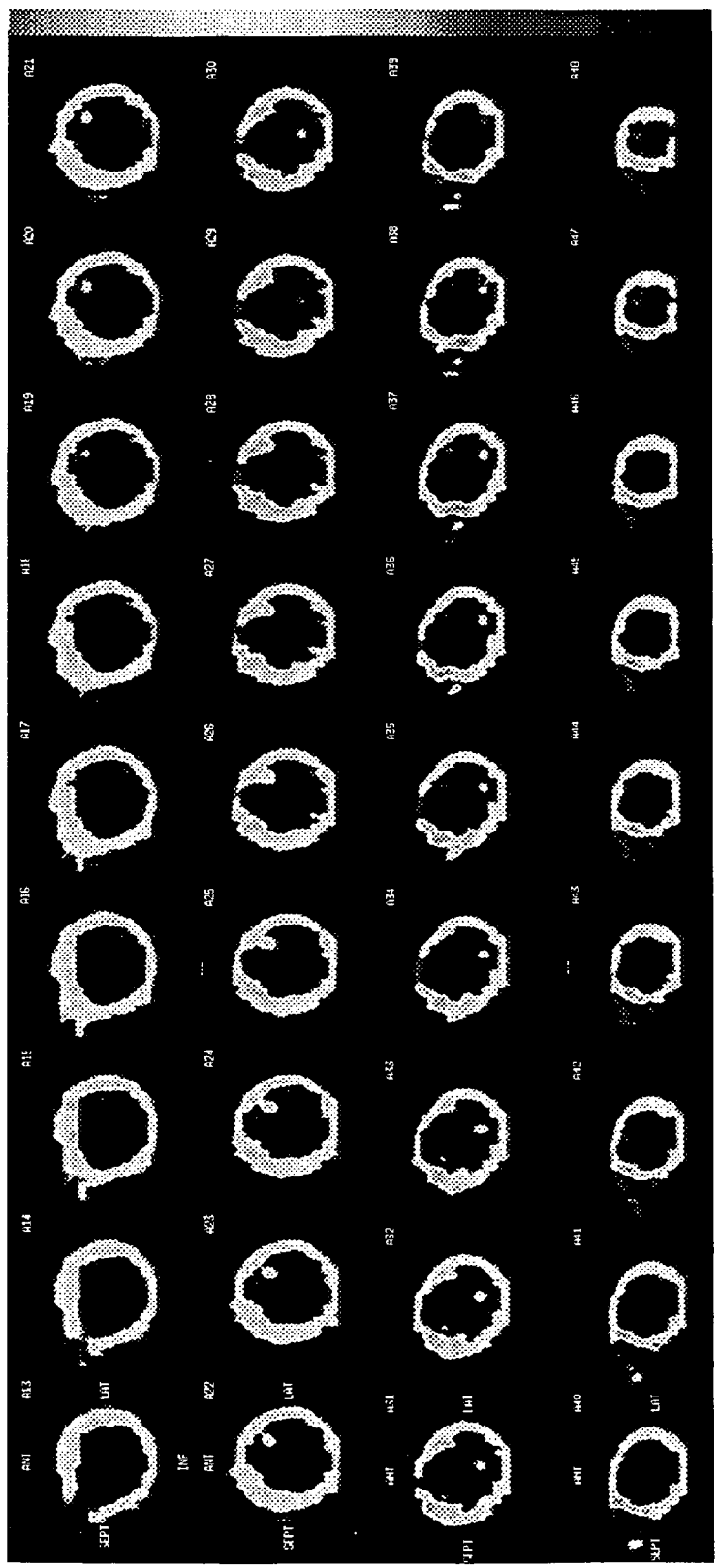
FIG. 8 is a diagram illustrating an oblique cross-sectional image example obtained by the cross-section conversion processing of a myocardial perfusion image using the X-ray CT apparatus illustrated in FIG. 1.

FIG. 8 is a diagram illustrating an oblique cross-sectional image example obtained due to the cross-section conversion processing of a myocardial perfusion image using the X-ray CT apparatus illustrated in FIG. 1.

The myocardium has an ellipsoidal shape including long and short axes, so converting the myocardial perfusion image into a circular cross-sectional image of which axis is in the longitudinal direction of the myocardium contributes to facilitating diagnosis, as illustrated in FIG. 8.

Furthermore, convenience at the time of diagnosis can be improved by synthesizing the myocardial perfusion image with the myocardial image for display. In this case, as for the myocardial image to be synthesized with the myocardial perfusion image, employing the high-resolution myocardial image prior to the matrix reduction processing in Step S4 and the addition of the contrast CT values between slices in Step S3 is more effective.

Consequently, in Step S8, the image synthesizing unit 24g receives the high-resolution myocardial image prior to the matrix reduction processing and the addition of the contrast CT values between slices from the image acquisition unit 24a, and generates an image synthesized with the myocardial perfusion image.

Figure 9:
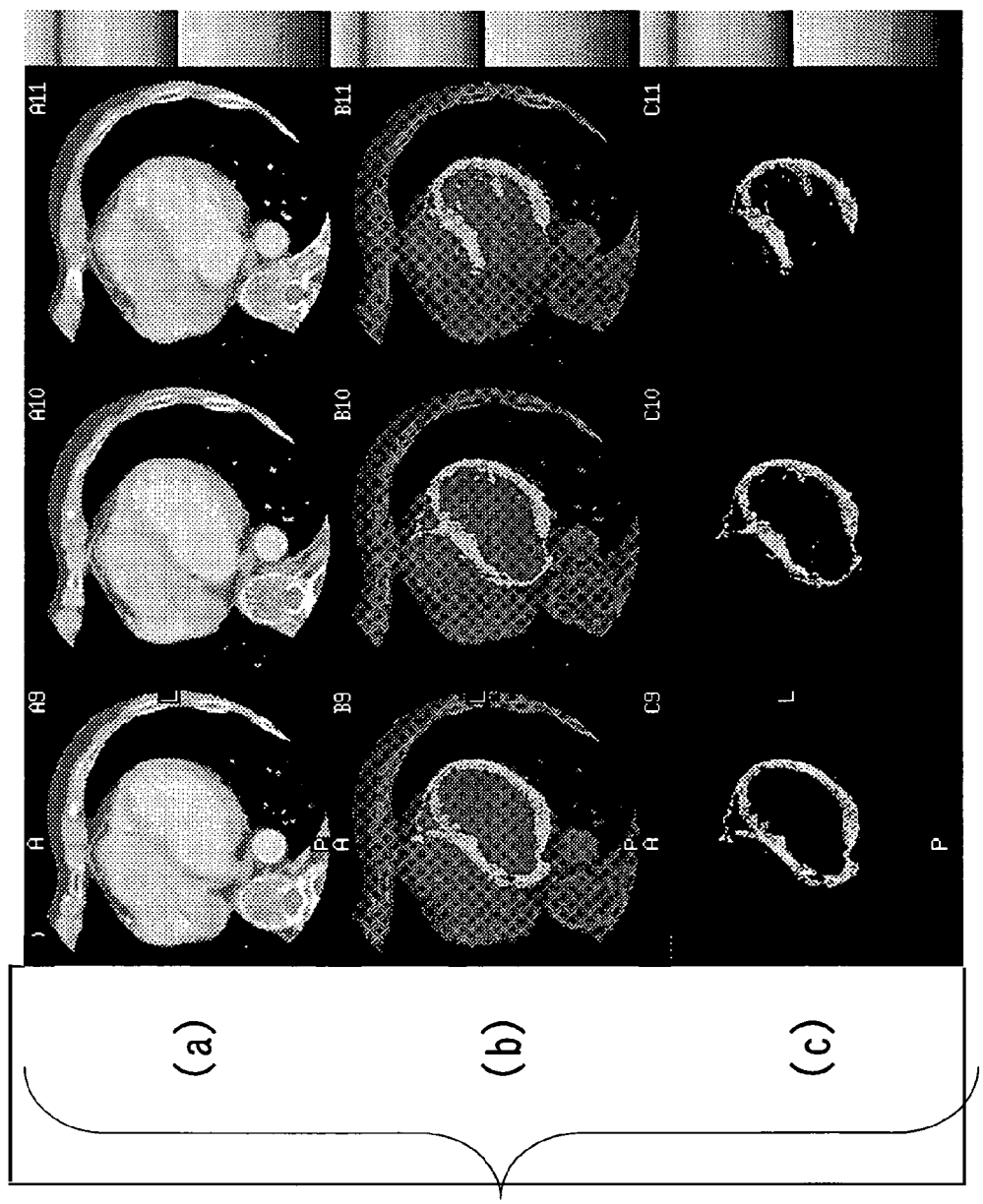
FIG. 9 is a diagram illustrating an image example obtained by synthesizing a myocardial perfusion image with a myocardial image using the X-ray CT apparatus illustrated in FIG. 1.

FIG. 9 is a diagram illustrating an image example obtained by synthesizing a myocardial perfusion image with a myocardial image using the X-ray CT apparatus illustrated in FIG. 1.

In FIG. 9, (a) is the high-resolution myocardial image prior to the matrix reduction processing and the addition of the contrast CT values between slices, which is obtained by the image acquisition unit 24a, and (c) is the myocardial perfusion image obtained from the myocardial image following the resolution reduction processing. The fusion image indicating the myocardium and the blood flow such as shown in (b) can be obtained by synthesizing the high-resolution myocardial image shown in (a) with the low-resolution myocardial perfusion image shown in (c). Thus, synthesizing the myocardial image with the blood flow image facilitates diagnosis.

The respective images such as the blood flow image generated by the blood-flow image generating unit 24e, the oblique cross-sectional image generated by the oblique cross-section converting unit 24f, and the synthesized image generated by the image synthesizing unit 24g are provided to the display processing unit 24h. Subsequently, the display processing unit 24h provides image signals for displaying each image to the image display unit 16 so as to display the image signals.

Now, the user can instruct automatic setting of display conditions for displaying each image through the input unit 17. The display processing unit 24h provides image signals for displaying an electronic button to the image display unit 16, for example.

Figure 10:
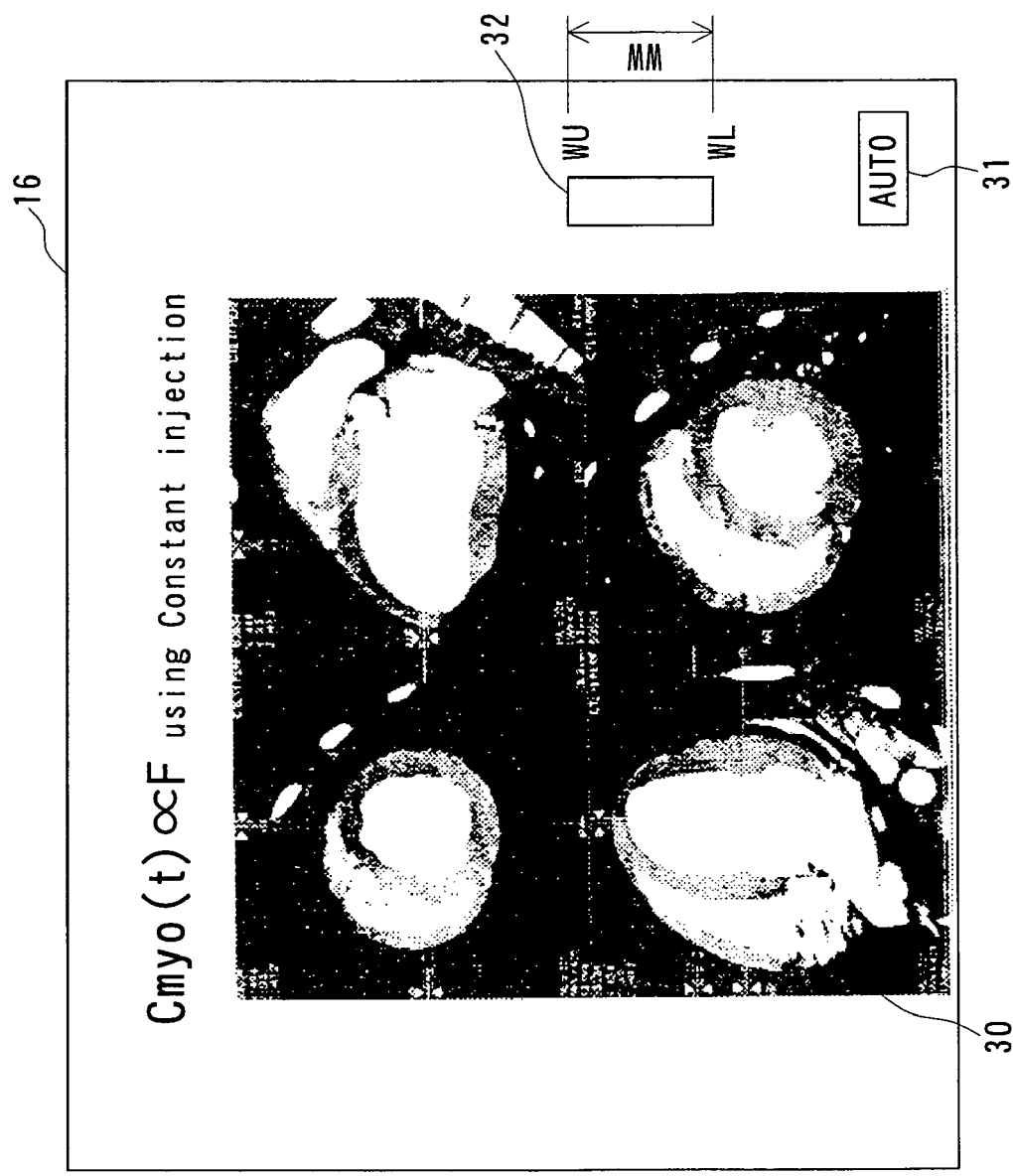
FIG. 10 is a diagram illustrating a blood flow image example displayed on the image display unit of the X-ray CT apparatus illustrated in FIG. 1 by automatically setting display conditions.

FIG. 10 is a diagram illustrating a blood flow image example displayed on the image display unit of the X-ray CT apparatus illustrated in FIG. 1 by automatically setting display conditions.

As illustrated in FIG. 10, a contrast CT image 30, an automatic (AUTO) button 31 for instructing automatic setting of display conditions, and a luminance scale 32 are displayed on the screen of the image display unit 16. That is to say, FIG. 10 illustrates an example in the case of displaying the blood flow image by luminance so as to recognize the image through the grayscale.

Upon the user pressing the automatic (AUTO) button 31 by operating the input unit 17, the input unit 17 provides the automatic setting instructions of display conditions to the display processing unit 24h. In response to the instructions, the display processing unit 24h sets an appropriate value to an upper limit value WU and lower limit value WL of the luminance scale (window level), and the a width of window level WW between upper limit value and lower limit value to display a blood flow image automatically.

More specifically, let us say that the myocardial CT value (34 or so) is A, the concentration of the contrast medium Cmyo(t) within the myocardial portion is B, and an arbitrary value for fine adjustment is β, settings such as WU=A+B and WL=A+β (accordingly, WW=B−β), or WL=A+β and WW=A+β+B can be performed. Consequently, the luminance scale is set to a value appropriate for displaying the blood flow image of the myocardial portion, and the myocardial blood flow image is displayed in grayscale by luminance as illustrated in FIG. 10.

At this time, values other than the values between WU and WL are removed by conversion into certain luminance such as black. Alternatively, different gradation conversion properties are provided to the portion between WU and WL and the portion other than between WU and WL so as to emphasize the values between WU and WL for the perspective of display. Note that, preferably, performing the gradation conversion processing so as to display the portion of the value WL in black (luminance value zero or extremely low luminance value) allows the user to visually recognize less blood flow portions.

Note that in FIG. 10, the myocardial blood flow image is displayed with the other images being superimposed thereon. An arrangement may be made wherein the values for determining display conditions, such as A, B, and β, can be adjusted finely by operating the input unit 17. The value of A is not restricted to the CT value, and rather may be changed according to clinical purposes. The value B may be determined experientially as a default value.

In addition to this, displaying the range between WU and WL in color may allow the user to visually recognize the blood flow image of the myocardial portion. In the event of performing color display, gradation of color display may be divided into 16 stages visually, or may be divided into 16 stages or more, or 16 stages or less, according to stages to be recognized, for example.

The automatic (AUTO) button 31 may be displayed in the event of activating a specific application for performing myocardial blood flow display or myocardial blood flow analysis, and the like by utilizing an application program for executing image display processing, for example. Alternatively, a hardware key made up of specific hardware may be provided on the input unit 17 as the automatic (AUTO) button 31.

In addition to the procedures shown in the flowchart in FIG. 5, the sequence of each step may be changed, or a part of the steps may be omitted so as to generate a myocardial perfusion image. Examples include procedures: S1→S2→S3→S4→S6→S7→S5→S8, procedures: S1→S2→S7→S6→S8, and procedures: S1→S2→S7→S3→S4→S5→S6→S8.

With the X-ray CT apparatus 1 and myocardial perfusion image generating system 24 thus configured, coronary artery contrast CT data and myocardial contrast CT data, which are collected due to continuous injection of a contrast medium under a certain condition, include information regarding myocardial perfusion serving as the index of blood flow perfusion within the myocardial portion, so that image formation is performed by extracting information regarding myocardial perfusion from the coronary artery contrast CT data and myocardial contrast CT data through data processing. More specifically, the X-ray CT apparatus 1 and myocardial perfusion image generating system 24 perform static injection of a contrast medium into the subject P, acquire a myocardial contrast CT image during a period in which the contrast medium flows within the myocardial portion and coronary artery at the constant concentration Ca(t), and consider the distribution image of contrast medium components as a blood flow perfusion image indicating the relative blood perfusion F, since the distribution image of the contrast medium components to be obtained by subtracting the CT value of the myocardium from the acquired myocardial contrast CT image has a relation proportional to the blood flow perfusion F.

Accordingly, the X-ray CT apparatus 1 and the myocardial perfusion image generating system 24 generate a myocardial perfusion image in shorter a period while further reducing the contrast medium injection rate as to the subject and dosage due to X-rays. In other words, heretofore, scanning for acquiring a myocardial image and scanning for acquiring blood flow information have been performed independently, but the X-ray CT apparatus 1 and myocardial-perfusion image generating system 24 can acquire blood flow information from information, such as the coronary artery contrast CT image data, myocardial contrast CT image data, and the like, obtained by the scanning for acquiring a myocardial image without adding the scanning for acquiring the blood flow information. Consequently, a myocardial perfusion image can be generated in a shorter period while reducing the X-raying period of the subject and the injection amount of the contrast medium due to reduction in the number of times of scanning.

Furthermore, a myocardial perfusion examination due to CT, which have been conventionally impossible in a routine examination, become available, so that the present invention allows the user to determine patient treatment policy quickly by a CT examination alone in the case of emergency due to heart disease.

Note that with the aforementioned embodiment, a blood flow image has been generated by subtracting the CT value of the myocardium alone from the myocardial contrast CT image data, but a blood flow image may be generated by subtracting a value obtained by adding/subtracting/multiplying/dividing a certain value as to the CT value of the myocardium, i.e., a certain value obtained from the CT value of the myocardium from the myocardial contrast CT image data.

What is claimed is:

1. An X-ray CT apparatus comprising:
an X-ray tube for radiating X-ray to a subject so as to scan the subject;
an X-ray detector for detecting the radiated X-ray;
a reconstruction unit for reconstructing an image within the subject based on an obtained projection data;
a contrast-medium injector controlling unit configured to control an injector so that the injector continuously injects a contrast medium into a subject by controlling the injector to inject the contrast medium at a first speed for a first time interval and to inject the contrast medium at a second speed for a second time interval following the first time interval, to obtain a state in which a concentration of the contrast medium in a myocardial portion of the subject is considered to be at a preset desired constant value;
an image generating unit configured to generate the image based on the projection data once in the state in which the concentration of the contrast medium in the myocardial portion of the subject is considered to be at the preset desired constant value; and
a blood-flow image generating unit configured to generate a blood flow image representing a blood flow rate in myocardium by removing components of a myocardial tissue from a portion of a myocardial region of the image generated by the image generating unit.

2. An X-ray CT apparatus according to claim 1, further comprising a determining region unit configured to determine the portion of the myocardial region of the image generated by the image generating unit, wherein the blood-flow image generating unit is configured so as to remove the components of the myocardial tissue from the portion of the myocardial region determined by the determining region unit.

3. An X-ray CT apparatus according to claim 1, wherein the image generating unit is configured to generate the blood flow image by subtracting a CT value equivalent to the myocardium from a CT image of the portion of the myocardial region.

4. An X-ray CT apparatus according to claim 1, further comprising a display processing unit configured to set a value of a window level at the time of performing at least either gradation conversion processing and color tone conversion processing based on a value corresponding to the myocardial portion contrasted by the contrast medium and a value corresponding to the myocardium.

5. An X-ray CT apparatus according to claim 1, further comprising a display processing unit configured to set a value of a window level at a time of performing at least either gradation conversion processing and color tone conversion processing so as to emphasize pixels having a value between a value corresponding to the myocardial portion contrasted by the contrast medium and a value corresponding to the myocardium.

6. An X-ray CT apparatus comprising:
an X-ray tube for radiating X-ray to a subject;
an X-ray detector for detecting the radiated X-ray;
a reconstruction unit for reconstructing an image within the subject based on an obtained projection data;
a contrast-medium injector controlling unit configured to control an injector so that the injector continuously injects a contrast medium into a subject by controlling the injector to inject the contrast medium at a first speed for a first time interval and to inject the contrast medium at a second speed for a second time interval following the first time interval, and to obtain a state in which a concentration of the contrast medium in a myocardial portion of the subject is considered to be at a preset desired constant value;
an image collection unit configured to collect a contrast CT image synchronously with an electrocardiogram once in a period in which the concentration of the contrast medium in the myocardial portion is considered to be at the preset desired constant value; and
a blood-flow image generating unit configured to generate a blood flow image representing a blood flow rate in myocardium by subtracting a CT value of the myocardium from the contrast CT image data of the myocardial portion.

7. An X-ray CT apparatus according to claim 6, wherein the blood-flow image generating unit is configured to obtain a correction coefficient based on a temporal change rate of the concentration of the contrast medium with a coronary artery in an event that the temporal change rate of the concentration of the contrast medium with the coronary artery can be considered to be constant, and so as to correct a CT value of the blood flow image due to the obtained correction coefficient.

8. An X-ray CT apparatus according to claim 6, further comprising an oblique cross-section converting unit configured to generate a cross-sectional image in an arbitrary cross-section by converting a cross-section of the blood flow image.

9. An X-ray CT apparatus according to claim 6, further comprising a slice-thickness adder unit configured to reduce a resolution of the contrast CT image data in a slice direction by adding contrast CT values between adjacent slices of the contrast CT image data.

10. An X-ray CT apparatus according to claim 9, further comprising an image synthesizing unit configured to synthesize and superimpose a blood flow image generated from the contrast CT image data having a reduced resolution with the contrast CT image data having resolution prior to be reduced so as to be displayed at a same position on a screen with adjusting an arbitrary value such as transparency of both of the images.

11. An X-ray CT apparatus according to claim 6, further comprising a matrix reduction unit configured to reduce a resolution by subjecting contrast CT values of the contrast CT image data to either adding or averaging to reduce matrix size.

12. An X-ray CT apparatus according to claim 11, further comprising an image synthesizing unit configured to synthesize and superimpose a blood flow image generated from the contrast CT image data having a reduced resolution with the contrast CT image data having resolution prior to being reduced so as to be displayed at a same position on a screen with adjusting an arbitrary value such as transparency of both of the images.

13. A myocardial perfusion image generating system comprising:
a contrast-medium injector controlling unit configured to control an injector so that the injector continuously injects a contrast medium into a subject by controlling the injector to inject the contrast medium at a first speed for a first time interval and to inject the contrast medium at a second speed for a second time interval following the first time interval, and to obtain a state in which a concentration of the contrast medium in a myocardial portion of the subject is considered to be at a preset desired constant value;
an image acquisition unit configured to acquire an image once in the state in which the concentration of the contrast medium in the myocardial portion of the subject is considered to be at the preset desired constant value; and a blood-flow image generating unit configured to generate a blood flow image representing a blood flow rate in myocardium by removing components of a myocardial tissue from a portion of the myocardial region of the image acquired by the image acquisition unit.

14. A myocardial perfusion image generating system comprising:

a contrast-medium injector controlling unit configured to control an injector so that the injector continuously injects a contrast medium into a subject by controlling the injector to inject the contrast medium at a first speed for a first time interval and to inject the contrast medium at a second speed for a second time interval following the first time interval, and to obtain a state in which a concentration of the contrast medium in a myocardial portion of the subject is considered to be at a preset desired constant value;

an image acquisition unit configured to acquire contrast CT image data collected synchronously with an electrocardiogram once in the state in which the concentration of the contrast medium in the myocardial portion of the subject is considered to be at the preset desired constant value; and a blood-flow image generating unit configured to generate a blood flow image representing a blood flow rate in myocardium by subtracting a CT value of the myocardium from the contrast CT image data acquired by the image acquisition unit.

* * * * *